(12) United States Patent
Messina

(10) Patent No.: US 6,372,240 B1
(45) Date of Patent: Apr. 16, 2002

(54) DEER REPELLENT AND METHOD

(76) Inventor: James Messina, 58 Califon Rd., Long Valley, NJ (US) 07853

( * ) Notice: Subject to any disclaimer, the term of this patent is extended or adjusted under 35 U.S.C. 154(b) by 0 days.

(21) Appl. No.: 09/668,860

(22) Filed: Sep. 25, 2000

(51) Int. Cl.⁷ .............................................. A61K 35/78
(52) U.S. Cl. ...................... 424/405; 424/407; 424/412; 424/417; 424/581; 424/745; 424/747
(58) Field of Search ................................. 424/405, 407, 424/409, 412, 417, 581, 745, 747

(56) References Cited

U.S. PATENT DOCUMENTS 5,183,661 A * 2/1993 Messina

OTHER PUBLICATIONS

Harris et al. HortScience, (Jun. 2000) vol. 35, No. 3, pp. 466–467.*

* cited by examiner

*Primary Examiner*—Francisco Prats
*Assistant Examiner*—Susan D. Coe
(74) *Attorney, Agent, or Firm*—Graham, Curtin & Sheridan; Richard T. Laughlin, Esq.

(57) ABSTRACT

A deer repellent formulation and method for warding off a deer from a shrub or plant. The formulation is an admixture of water, Rosemary oil emulsion, mint oil emulsion, a thickener, white distilled vinegar and dry eggs. The formulation can be applied to a support medium such as clay or a length of rope and then associated with the vegetation to be protected. The formulation can also be formed into a viscous composition and used in containers near the vegetation to be protected.

5 Claims, No Drawings

DEER REPELLENT AND METHOD

The invention generally relates to a deer repellent, and in particular the invention relates to a deer repellent composition which is transparent and can be applied to a wide range of surfaces and to a method for the use of such a composition.

BACKGROUND OF THE INVENTION

The prior art deer repellent formulation is described in U.S. Pat. No. 4,965,070, issued Oct. 23, 1990 to the same inventor as this application. The prior art formulation consisted essentially of, by volume, 68 to 90% water; 6 to 10% thiram; 0.5 to 2% chicken eggs; 1 to 2% liquid hot sauce; 2 to 16% adhesive to aid in adhering to vegetation; and 0.5 to 2% coloring dye. The dye is necessary so the coating will blend in with the foliage.

One problem of the prior art deer repellent formulation is that, although the ingredients are common materials, it requires approval of the Environmental Protection Agency ("EPA") which involves long and costly tests. Formulations of this type are applied by small companies, such as landscape gardeners, and the obtaining of approval from the EPA is financially prohibitive. This results in widespread destruction of homeowners' landscaping because of the unfettered proliferation of deer in suburban areas. Further, the prior art materials have a limited effective life and the odor of the formulation can limit its acceptance. A further problem with the prior art compositions is that they require a colorant to hide their presence on the foliage.

OBJECTS OF THE INVENTION

One object of the present invention is to provide an improved deer repellent formulation for application to a shrub, plant or the like which can be acceptable under EPA regulations.

Another object of the invention is to provide a deer repellent formulation more acceptable to humans.

Another object of the invention is to make use of EPA-approved components without reduction of the effectiveness of the treatment.

A still further object is to provide such a composition which is transparent.

Other objects and the advantages of the invention will appear from the following description.

SUMMARY OF THE INVENTION

According to the present invention, a non-toxic deer repellent formulation and method for its use are provided. The formulation is an aqueous solution or mixture consisting essentially of water and a composition comprising 5 to 20 ounce of Rosemary oil emulsion, 5 to 20 ounces of mint oil emulsion, zanthan gum as a thickener and sufficient water to make one gallon (128 ounces). If desired, the formulation can be modified by adding 10 to 30 ounces of white distilled vinegar, 10 to 30 ounces of dry eggs and one to fifteen teaspoons of table salt. The thickener can be added to give the composition the desired application characteristics. Typical would be 1 to 5% of the total composition of thickener. All of the percentages are by volume of the composition.

Prior to application to vegetation, the composition is diluted in a concentration of one part of repellant to approximately 5 to 15 parts water. The mixture is stirred until a uniform composition is obtained. The composition is sprayed with a fine nozzle power spray, on the foliage to be protected in about one gallon for each 35,000 square feet of foliage.

As an alternate procedure the composition can be impregnated into a rope with the rope being placed around the vegetation to be protected.

DESCRIPTION OF THE PREFERRED EMBODIMENT

The preferred deer repellent formulation is an aqueous solution or mixture consisted essentially of water and a composition comprising 10 ounces of Rosemary oil emulsion, 10 ounces of mint oil emulsion, Zanthan gum as a thickener and sufficient water to make one gallon (128 ounces). If desired, the formulation can be modified by adding 20 ounces of white distilled vinegar, 20 ounces of dry eggs and a 10 teaspoons of table salt. In certain instances, when weather conditions are dry, a preservative such as potassium sorbate can be used. The thickener can be added to give the composition the desired application characteristics. Typical would be 1 to 5% of the total composition of thickener. All of the percentages are by volume of the composition. In some instances where greater adherence to the foliage is desired, a sticker such as the material sold under the trademark "Nu Film P" can be added. As an alternative, "CLEARSPRAY" or the like can be used. In particular, the adhesive is used for a deer repellent assembly, which is exposed to substantial amounts of rain or snow.

The composition of the invention can be utilized in the manner described in U.S. Pat. No. 5,183,661 issued on Feb. 2, 1993 to James Messina. The formulation of the invention can be applied to a support medium such as a solid braid, number 8, cotton and polyester, one-quarter inch diameter, sash cord rope of 100 foot length, which is sold by the Lehigh Group, Allentown, Pa. 18105, USA. The support medium can also be a clay material, which ranges in size of clay granules or particles, from dustless fine granules to about one-quarter inch overall diameter or thickness granules. The clay material comes packaged in a 0.20 pound bag, which is made of a finely woven cloth material and which has a drawstring along an open top edge thereof, and which has a size of about 4 inches in height by about 3 inches in width when flat. The drawstring threads through spaced holes located about one-half inch down from the bag top edge.

The deer repellent assembly of support rope and formulation can be wrapped around a shrub or plant or strung between shrubs and plants. The deer repellent assembly of support medium clay material and formulation can be distributed under and around shrubs and plants or the like.

It is noted that 16 fluid ounces of deer repellent formulation is sufficient to wet the 100 foot length of one-quarter inch diameter rope. Also, eleven fluid ounces of deer repellent formulation is sufficient to wet throughout the one pound of clay granules. A shorter rope length requires proportionally less fluid ounces of formulation based upon rope length and rope cross section areas. Less than one pound of clay granules medium requires proportionally less fluid ounces of formulation based upon medium volume.

The deer repellant formulation can also be prepared for addition to a container having sufficient holes or openings to allow the deer to lick the container and come in contact with the repellant formulation. The fluid deer repellant formulation is admixed with wheat flower and corn cob grounds to form a semi solid composition and then poured into the container having openings.

The following examples are given for purposes of illustration and not by way of limitation.

EXAMPLE 1

The deer repellant formulation in the preferred embodiment for outdoor application as follows:

10 ounces of Rosemary oil emulsion 10 ounces of mint oil emulsion

Water is added to make one gallon of mixture to make a concentrate which can be diluted with water on the job site and applied to the foliage in a fine mist from a power spray.

EXAMPLE 2

The deer repellant formulation of Example 1 can have added:

20 ounces of white distilled vinegar 10 ounces of table salt 20 ounces of dried chicken eggs.

EXAMPLE 3

The deer repellant formulation of Example 2 with the addition of potassium sorbate as a preservative.

EXAMPLE 4

The deer repellant formulation of Example 2 with the addition of 1 to 10 ounce of zanthan gum as a thickener.

EXAMPLE 5

The deer repellant formulation of Example 2 with the addition of 5 ounce of "Nu-Film P" as a sticker to aid in the adherence of the formulation to the foliage.

EXAMPLE 6

The composition of Example 2 is formed into a solid medium by mixing the following:

2 cups of wheat flower 2 cups of ground up corn cobs 2 cups of the formula of Example 2.

The composition is mixed uniformly and then added to a container with holes. The size of the container is 1 inch in diameter by 2 inch in length. The container is hung or tied to the plant to be protected or elevated on a post adjacent to the plant.

EXAMPLE 7

The deer repellent composition of Example 2 is utilized as follows:

a 100 foot length of support rope of one-quarter inch diameter, and of cotton and polyester, solid braid material;

16 fluid ounces of deer repellent formulation of Example 2 is placed in a container. The deer repellent formulation is distributed evenly along the support rope length by dipping the rope into the container.

EXAMPLE 8

The deer repellent formulation of Example 1 is admixed as follows:

one pound by weight of clay granules in a particle size distribution from dustless fine particles to about one-quarter inch overall thickness particles for a support medium; eleven fluid ounces of deer repellent formulation of Example 1.

The deer repellent formulation is mixed with the support medium clay granules.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. The method of forming a deer repellant material which comprises mixing wheat flower with ground corn cobs, adding a mixture of Rosemary oil emulsion, mint oil emulsion and a thickener, blending the mixture and placing in a ventilated container and the placing the container in the vicinity of the foliage to be protected.

2. The method of claim 1 wherein the composition contains in addition dried chicken eggs and an adhesive.

3. The method of claim 1 wherein the composition is applied to a support medium in place of the container.

4. The method of claim 3 wherein the support medium is a braided rope of about one-quarter inch in diameter.

5. The method of claim 3 wherein the support medium is a volume of clay granules.

* * * * *